United States Patent
Nishitani et al.

(10) Patent No.: US 7,462,174 B2
(45) Date of Patent: Dec. 9, 2008

(54) SANITARY NAPKIN

(75) Inventors: Kazuya Nishitani, Kagawa (JP);
Toshiyuki Tanio, Kagawa (JP);
Masataka Kinoshita, Kagawa (JP);
Akane Sakai, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 239 days.

(21) Appl. No.: 10/862,926

(22) Filed: Jun. 7, 2004

(65) Prior Publication Data

US 2004/0260262 A1 Dec. 23, 2004

(30) Foreign Application Priority Data

Jun. 20, 2003 (JP) .............................. 2003-177366

(51) Int. Cl.
*A61F 13/15* (2006.01)
(52) U.S. Cl. ............................ 604/385.27; 604/385.04; 604/385.28
(58) Field of Classification Search ............ 604/385.04, 604/385.24–385.28
See application file for complete search history.

(56) References Cited

U.S. PATENT DOCUMENTS

| | | | | |
|---|---|---|---|---|
| 5,342,342 A * | 8/1994 | Kitaoka | ................. | 604/385.19 |
| 5,776,121 A * | 7/1998 | Roe et al. | ............... | 604/385.25 |
| 6,440,117 B1 * | 8/2002 | Itoh et al. | ............... | 604/385.28 |
| 6,569,140 B1 * | 5/2003 | Mizutani et al. | ....... | 604/385.28 |
| 7,056,311 B2 * | 6/2006 | Kinoshita et al. | ...... | 604/385.04 |
| 2004/0249355 A1 * | 12/2004 | Tanio et al. | ............ | 604/385.01 |
| 2004/0260262 A1 * | 12/2004 | Nishitani et al. | ....... | 604/385.04 |

FOREIGN PATENT DOCUMENTS

| | | | |
|---|---|---|---|
| JP | 08-280735 | A1 | 10/1996 |
| JP | 11-178852 | A1 | 7/1999 |
| JP | 2000-262555 | A1 | 9/2000 |
| JP | 2001-145667 | | 5/2001 |
| JP | 2001-293031 | | 10/2001 |
| JP | 2002-000656 | | 1/2002 |
| JP | 2002-165836 | A1 | 6/2002 |
| JP | 2003-180736 | A1 | 7/2003 |
| JP | 2003-210525 | A1 | 7/2003 |

* cited by examiner

*Primary Examiner*—Tatyana Zalukaeva
*Assistant Examiner*—Lynne Anderson
(74) *Attorney, Agent, or Firm*—Darby & Darby P.C.

(57) ABSTRACT

A sanitary napkin has leakage preventing walls on a skin-side surface of a main body. The leakage preventing wall has a skin-contacting portion, of which an inner edge is fixed at an inner edge's front end and an outer edge is fixed at an outer edge's front end located forward of the inner edge's front end. Therefore, when the leakage preventing wall is in a rising position, the skin-contacting portion is inclined with the outer edge closer to the wearer's body than the inner edge. Accordingly, the skin-contacting portion can easily conform to the wearer's crotch on both sides of the vaginal opening.

10 Claims, 8 Drawing Sheets

SANITARY NAPKIN

BACKGROUND OF THE INVENTION

1. Field of the Invention

The present invention relates to a sanitary napkin comprising: a main body including a liquid absorbent layer; and leakage preventing walls extending longitudinally on a skin-side surface of the main body.

2. Description of the Related Art

In absorbent hygiene products, a main body is typically constructed to include a liquid-permeable topsheet, a liquid-impermeable backsheet and a liquid absorbent layer (absorbent core) disposed between the topsheet and the backsheet. Optionally, leakage preventing walls (cuffs) are disposed on a skin-side surface of the main body so as to prevent lateral leakage of liquid applied to the main body.

The leakage preventing wall is composed of: a sheet which is fixed to the skin-side surface of the main body to have a longitudinally extending base; and elastic members which are fixed to the sheet so as to longitudinally exert an elastic contractive force. With the elastic contractive force being exerted to bring front and rear portions of the main body closer to each other, the skin-side surface of the main body is concavely deformed, resulting in rising of the leakage preventing walls with their free ends moved away from the skin-side surface of the main body.

When employed in disposable diapers, the leakage preventing walls are typically constructed to rise obliquely inward so that the free ends are located closer to a longitudinal centerline of the diaper than the base, as disclosed in Japanese Unexamined Patent Publication No. 2001-293031 (Patent Publication 1) for instance. This is because disposable diapers are intended to receive a large amount of urine, as well as loose passage, at a time. With the leakage preventing wall rising obliquely inward, a pocket is formed between the skin-side surface of the main body and the leakage preventing wall, easily retaining the urine and loose passage. In addition, since the disposable diapers are of a relatively large width, the right and left leakage preventing walls can be located far away from each other. Accordingly, even when the inward leakage preventing walls fall to the skin-side surface of the main body, a relatively large area of the liquid absorbing region can remain exposed between the fallen leakage preventing walls.

On the other hand, sanitary napkins to be worn in the wearer's crotch are of a relatively small width. Accordingly, if the leakage preventing walls are disposed inward as in the diapers and fall to the skin-side surface of the main body due to contact with the crotch, they may extend to adjacent the vaginal opening, reducing the area substantially capable of absorbing liquid in the skin-side surface of the main body.

Consequently, the leakage preventing walls employed in the sanitary napkins are typically constructed to include: a rising portion that is allowed to rise from the skin-side surface of the main body; and a skin-contacting portion that is contiguous to an upper end of the rising portion and has an outwardly directed free end, as disclosed in Japanese Unexamined Patent Publication No. 2001-145667 (Patent Publication 2) and Japanese Unexamined Patent Publication No. 2002-656 (Patent Publication 3). When the sanitary napkins of this type are put on the crotch, the skin-contacting portions come into face-to-face contact with the crotch, thereby improving contact between the leakage preventing walls and the wearer's body. They are also aimed at preventing the area capable of absorbing liquid in the skin-side surface of the main body from being extremely reduced even when the skin-contacting portions fall to the skin-side surface due to contact with the crotch.

FIG. 11 is a schematic diagram showing a state where a conventional sanitary napkin 100 such as disclosed in Patent Publication 2 is put on the wearer's crotch.

The sanitary napkin 100 has a main body that is constructed to include a liquid-permeable topsheet 101, a liquid-impermeable backsheet 102 and a liquid absorbent layer 103 interposed therebetween. Fold-back flaps 104, 104 extend outwardly from transversely opposing sides of the main body. With the fold-back flaps 104, 104 being folded back along both side edges of a crotch part 110 of an undergarment and adhered to an outer surface of the crotch part 110, the sanitary napkin 100 can be positioned on the undergarment.

On right and left portions of the main body of the sanitary napkin 100, there are provided leakage preventing walls 105, 105. When no external force is exerted on the conventional sanitary napkin 100 such as disclosed in Patent Publication 2, skin-contacting portions 105a, 105a of the leakage preventing walls 105, 105 extend generally parallel with the skin-side surface of the main body with their outer edges 105a1, 105a1 directed transversely outward.

FIG. 11 also shows the crotch of a woman, wherein 121 represents the vaginal opening, 122 represents the labia majora, 123 represents the thigh, and 124 represents a narrow depression between the thigh 123 and the abdomen.

When the conventional sanitary napkin 100 comes into contact with the crotch and the thighs 123, 123, the skin-contacting portions 105a, 105a of the leakage preventing walls 105, 105 tend to be deformed with the outer edges 105a1, 105a1 moved downwardly, thereby forming spaces between the skin-contacting portions 105a, 105a and the wearer's body along the depressions 124, 124.

The sanitary napkin 100 is designed to absorb menstrual blood discharged from the vaginal opening 121 in the liquid absorbent layer 103, but when liquid absorbent layer 103 is given too much menstrual blood to absorb, it may flow down the crotch to leak out laterally. If spaces are formed between the skin-contacting portions 105a, 105a and the wearer's body, as set forth above, the menstrual blood flowing down the crotch tends to leak out beyond the skin-contacting portions 105a, 105a and reach the thighs 123, 123, causing the possibility that the undergarment will be stained with menstrual blood.

When the wearer is seated or sleeping, moreover, the menstrual blood having flown down the crotch tends to migrate farther anteriorly or posteriorly along the depressions 124, 124, easily causing rearward leakage of menstrual blood out of the sanitary napkin 100.

SUMMARY OF THE INVENTION

The present invention has been worked out in view of the shortcomings in the prior art set forth above. It is therefore an object of the present invention to provide a sanitary napkin effective in preventing lateral and rearward leakage of menstrual blood, in which leakage preventing walls raised from a main body can be kept in close contact with the wearer's crotch on both sides of the vaginal opening.

According to the present invention, there is provided a sanitary napkin comprising: an elongated main body having a skin-side surface and a garment-side surface and including a liquid absorbent layer; and a pair of leakage preventing walls disposed on the skin-side surface of the main body and extending longitudinally of the main body in parallel with each other, each leakage preventing wall being composed of a sheet and an elastic member for exerting an elastic contractive force on the sheet and including: a rising portion with a lower end fixed to the skin-side surface of the main body; and a skin-contacting portion contiguous to an upper end of the rising portion, the skin-contacting portion having transversely opposing outer and inner edges, the inner edge being located closer to a longitudinal centerline of the sanitary napkin than the outer edge, longitudinally opposing front and rear ends of the inner edge and longitudinally opposing front and rear ends of the outer edge being fixed to the skin-side surface of the main body, wherein a length between the front and rear ends of the outer edge is larger than a length between the front and rear ends of the inner edge, enabling the leakage preventing wall to rise with the outer edge moved farther away from the skin-side surface of the main body than the inner edge.

In the sanitary napkin, since the leakage preventing walls can rise with the skin-contacting portions inclined such that the outer edge is positioned farther away from the skin-side surface of the main body than the inner edge, the skin-contacting portions can easily conform to the woman's crotch on both sides of the vaginal opening. Hence, a space is hardly left between the skin-contacting portions and the crotch, preventing lateral leakage of menstrual blood.

In the present invention, the front end of the outer edge may be located farther forward than the front end of the inner edge, and the rear end of the outer edge may be located farther rearward than the rear end of the inner edge. With this construction, the skin-contacting portion can be easily inclined such that the outer edge is positioned farther away from the skin-side surface of the main body than the inner edge.

In order that the skin-contacting portion can be easily inclined, preferably, the length between the front and rear ends of the inner edge is 50 to 95% of the length between the front and rear ends of the outer edge. Also preferably, the skin-contacting portion includes longitudinally extending first and second elastic members, the first elastic member being located closer to the outer edge, the second elastic member being located closer to the inner edge, wherein when the main body is flattened, the first elastic member exerts a larger elastic contractive force than the second elastic member.

Along a straight line between the front end of the inner edge and the front end of the outer edge and along a straight line between the rear end of the inner edge and the rear end of the outer edge, the rising portion may be fixed in a folded state to the skin-side surface of the main body so that a fold line extends longitudinally over the whole rising portion. With this construction, the skin-contacting portion pushed down by contact with the wearer's crotch can be kept in an inclined position while descending to the main body. Accordingly, the skin-contacting portion can be kept in close contact with the wearer's crotch without causing a large amount of lateral displacement.

In the present invention, the upper end of the rising portion may be located intermediate the inner edge and the outer edge of the skin-contacting portion so that the skin-contacting portion has an inner portion extending from the upper end to the inner edge and an outer portion extending from the upper end to the outer edge. When the leakage preventing wall is in a rising position, the outer edge is preferably farther away from the skin-side surface of the main body than the upper end of the rising portion so that the outer portion is inclined. In this construction, the inner portions may be brought into face-to-face contact with the wearer's body on both sides of the vaginal opening, while the inclined outer portions may be brought into close contact with the depressions between the abdomen and the thighs. In this case, if the sheet is folded more times in the inner portion than in the outer portion, the outer portion may be inclined more than the inner portion. Preferably, the outer portion has a larger width than the inner portion so as to conform to the wearer's crotch.

BRIEF DESCRIPTION OF THE DRAWINGS

The present invention will be understood more fully from the detailed description given hereinafter and from the accompanying drawings of the preferred embodiments of the present invention, which, however, should not be taken to limit to the invention, but are for explanation and understanding only.

In the drawings.

DESCRIPTION OF THE PREFERRED EMBODIMENT

The present invention will be discussed hereinafter in detail in terms of the preferred embodiments according to the present invention with reference to the accompanying drawings. In the following description, numerous specific details are set forth in order to provide a thorough understanding of the present invention. It will be obvious, however, to those skilled in the art that the present invention may be practiced without these specific details. In other instances, well-known structures are not shown in detail in order not to obscure the features of the present invention.

It should be noted that the sanitary napkin, as well as its individual components, has two major surfaces: of which one surface intended to be worn toward the wearer's crotch is referred to as "skin-side surface", while the other surface is referred to as "garment-side surface". It should also be noted that unless otherwise stated, the term "length" as used herein refers to a dimension measured longitudinally of the sanitary napkin and the term "width" as used herein refers to a dimension measured transversely of the sanitary napkin.

Figure 1:
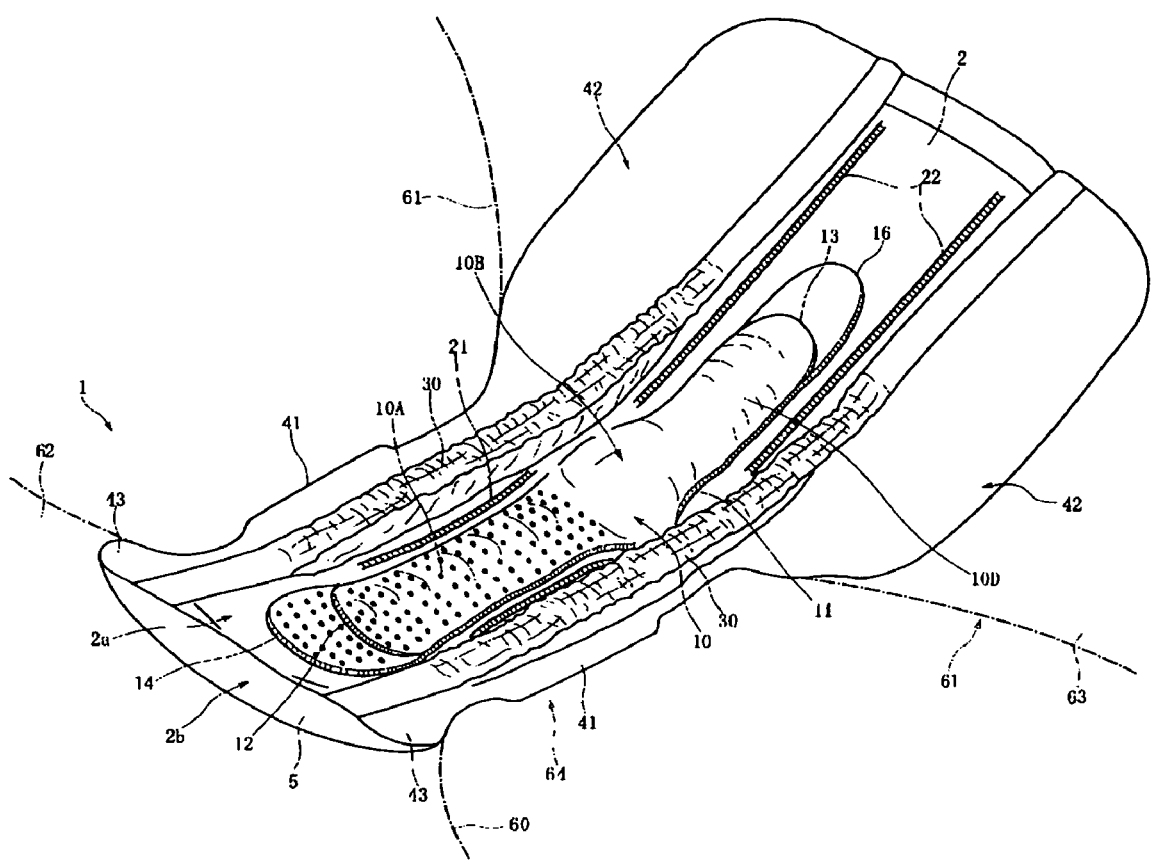
FIG. 1 is a perspective view showing a state where a sanitary napkin according to a first embodiment of the present invention is placed on an undergarment.
Figure 2:
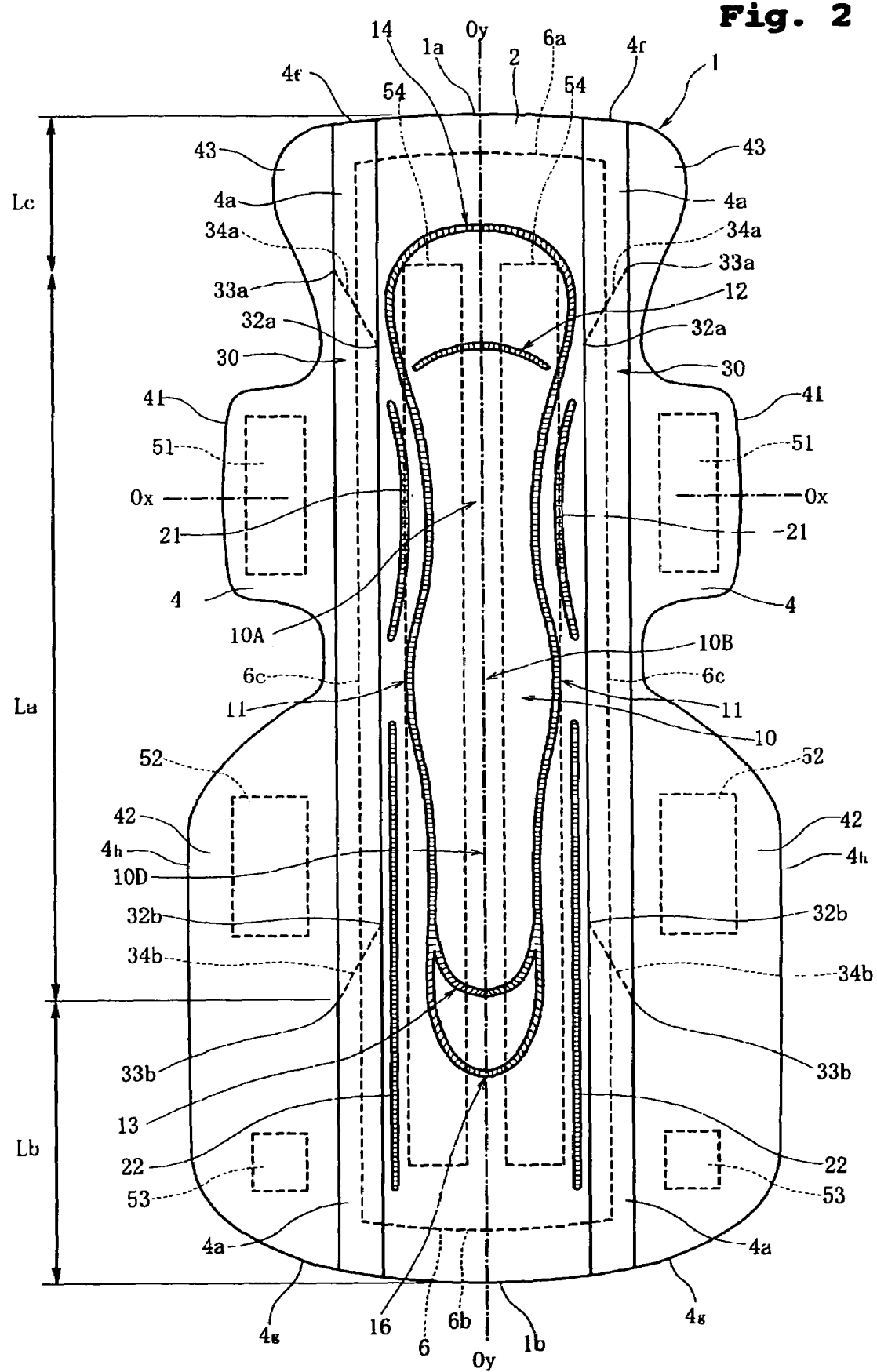
FIG. 2 is a top plan view of the sanitary napkin.
Figure 3:
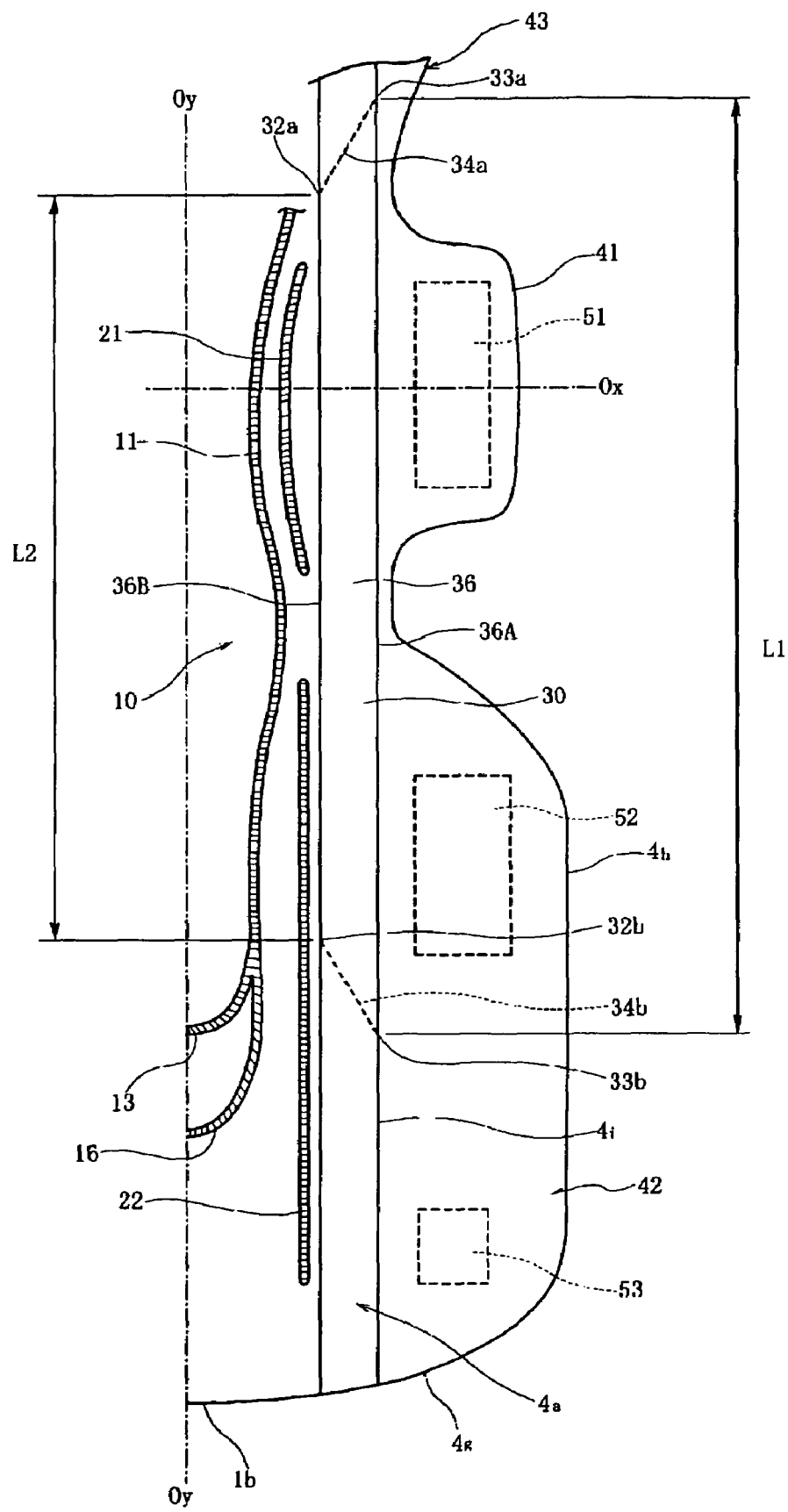
FIG. 3 is a top plan view showing a portion of the sanitary napkin on an enlarged scale.
Figure 4:
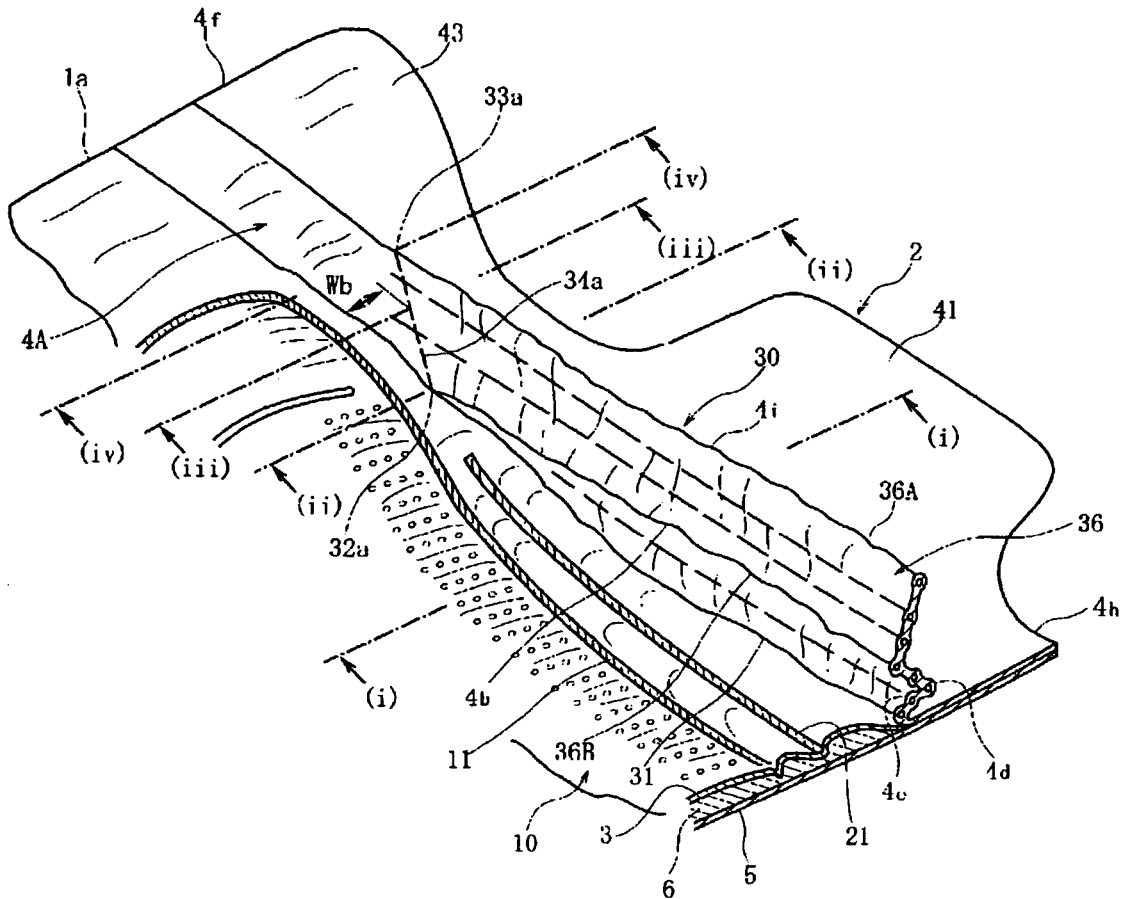
FIG. 4 is a perspective view showing a portion of a leakage preventing wall in a rising position.
Figure 5:
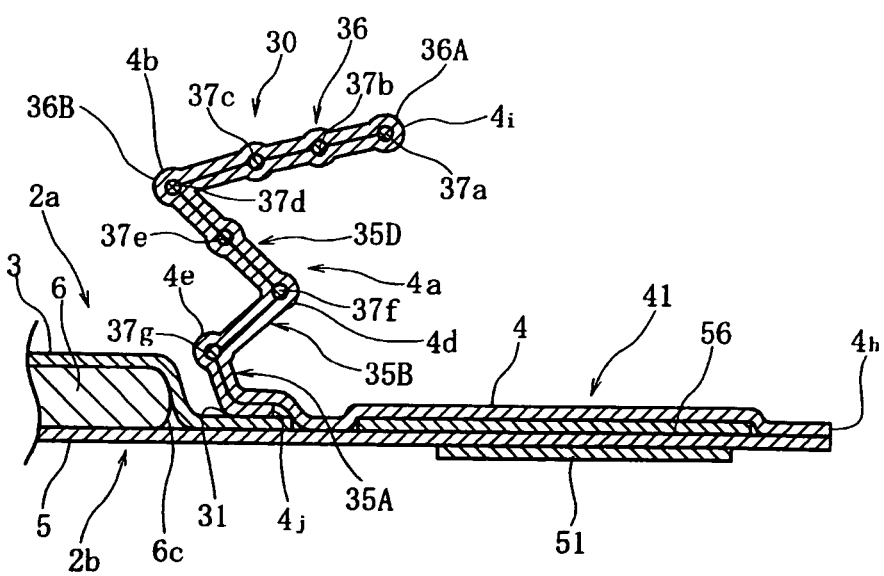
FIG. 5 is a sectional view taken along line (i)-(i) of FIG. 4.
Figure 6A:
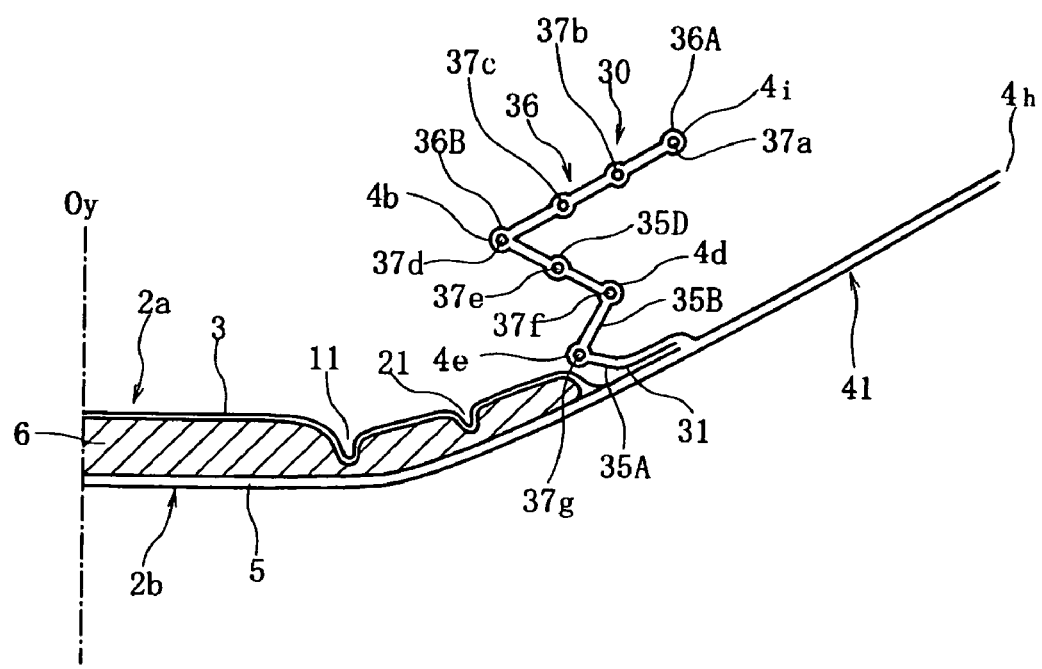
FIG. 6(A) is a schematic diagram showing a section taken along line (i)-(i) of FIG. 4
Figure 6B:
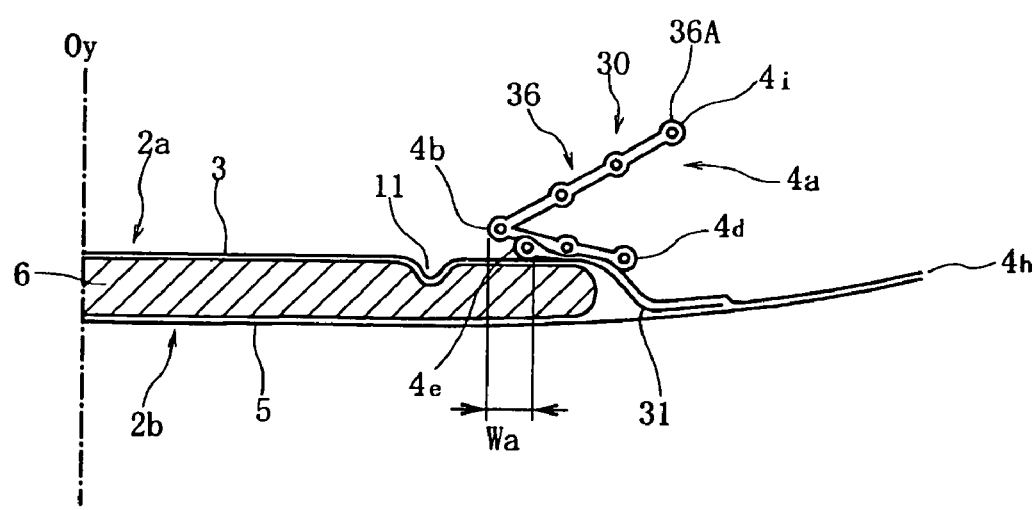
FIG. 6(B) is a schematic diagram showing a section taken along line (ii)-(ii) of FIG. 4.
Figure 7A:
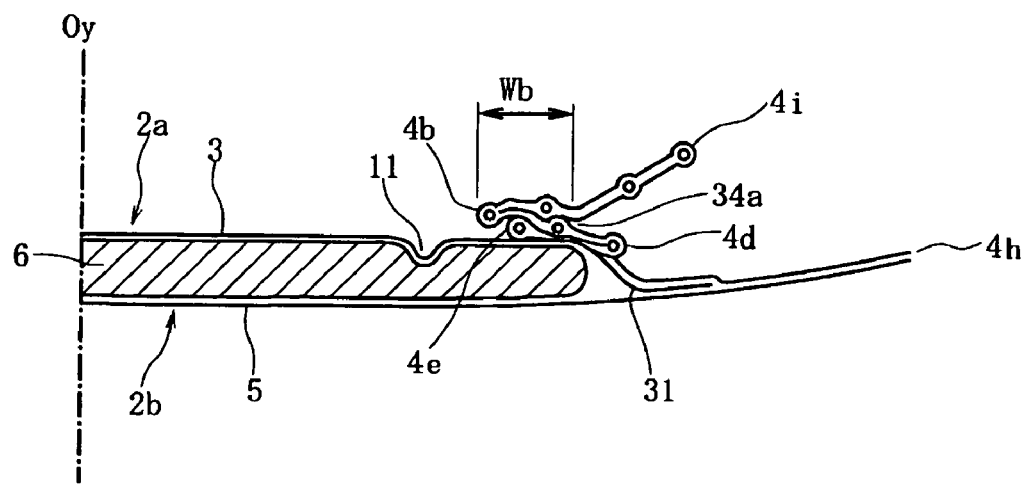
FIG. 7(A) is a schematic diagram showing a section taken along line (iii)-(iii) of FIG. 4
Figure 7B:
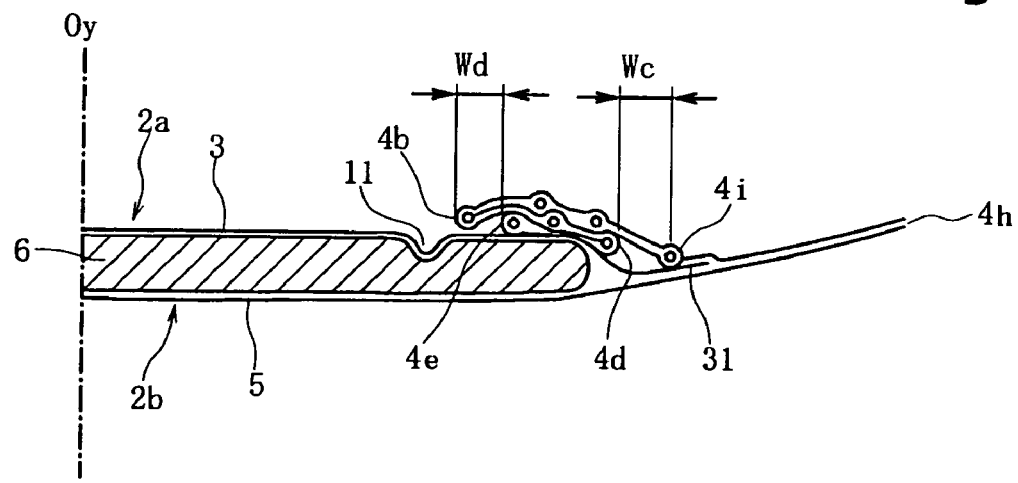
FIG. 7(B) is a schematic diagram showing a section taken along line (iv)-(iv) of FIG. 4.

FIG. 1 is a perspective view showing a state where a sanitary napkin 1 according to a first embodiment of the present invention is placed on an undergarment; FIG. 2 is a top plan view of the sanitary napkin 1; FIG. 3 is a top plan view showing a portion of the sanitary napkin 1 on an enlarged scale; FIG. 4 is a perspective view showing a portion of a leakage preventing wall in a rising position; FIG. 5 is a sectional view taken along line (i)-(i) of FIG. 4; FIG. 6(A) is a schematic diagram showing a section taken along line (i)-(i) of FIG. 4 and FIG. 6(B) is a schematic diagram showing a section taken along line (ii)-(ii) of FIG. 4; and FIG. 7(A) is a schematic diagram showing a section taken along line (iii)-(iii) of FIG. 4 and FIG. 7(B) is a schematic diagram showing a section taken along line (iv)-(iv) of FIG. 4.

The sanitary napkin 1 comprises: an elongated main body 2 having a skin-side surface 2a and a garment-side surface 2b; and a pair of leakage preventing walls 30, 30 that are allowed to rise from the skin-side surface 2a of the main body 2.

In FIG. 2, the sanitary napkin 1, which is slightly curved in FIG. 1, is shown in a fully opened (or flattened) state. FIG. 2 shows a longitudinal centerline Oy-Oy coinciding with midpoints of front and rear end edges 1a, 1b of the sanitary napkin 1, wherein the sanitary napkin 1 has bilateral symmetry about the longitudinal centerline Oy-Oy. FIG. 2 also shows a transverse reference line Ox-Ox perpendicular to the longitudinal centerline Oy-Oy. When the sanitary napkin 1 is worn, the intersection of the longitudinal centerline Oy-Oy and the transverse reference line Ox-Ox and its surrounding area may confront the woman's vaginal opening with the skin-side surface 2a directed to the woman's crotch.

As shown in FIG. 5, a liquid-permeable topsheet 3 appears on the skin-side surface 2a of the main body 2 in a region between the leakage preventing walls 30, 30; a side sheet 4 appears outside each leakage preventing wall 30. In the present embodiment, the side sheet 4 forms the leakage preventing wall 30. On the other hand, a liquid-impermeable backsheet 5 appears on the garment-side surface 2b of the main body 2.

The main body 2 has a liquid absorbent layer 6 disposed between the topsheet 3 and the backsheet 5. As shown in FIG. 2, the liquid absorbent layer 6 is of an almost rectangular shape. The liquid absorbent layer 6 has a front end edge 6a slightly inside the front end edge 1a of the sanitary napkin 1 and a rear end edge 6b slightly inside the rear end edge 1b of the sanitary napkin 1. As shown in FIG. 5, the liquid absorbent layer 6 has transversely opposite side edges 6c inside bases (or lower ends) 31 of the leakage preventing walls 30. However, the side edges 6c may be located outside the bases 31.

In the skin-side surface 2a, compressed grooves where the topsheet 3 and the liquid absorbent layer 6 are compressed are formed in the region between the leakage preventing walls 30, 30. The compressed grooves comprise: longitudinal compressed grooves 11, 11 extending longitudinally in a curved manner; a front transverse compressed groove 12 located between front portions of the longitudinal compressed grooves 11, 11; and a rear transverse compressed groove 13 connecting rear portions of the longitudinal compressed grooves 11, 11.

The region surrounded by the longitudinal compressed grooves 11, 11, the front transverse compressed groove 12, and the rear transverse compressed groove 13 is referred to as elongated main absorbent region 10. The main absorbent region 10 includes a front main absorbent region 10A, an intermediate main absorbent region 10B, and a rear main absorbent region 10D.

In the front main absorbent region 10A, the right and left longitudinal compressed grooves 11, 11 are curved toward the longitudinal centerline Oy-Oy, wherein the distance between the longitudinal compressed grooves 11, 11 is smallest near the transverse reference line Ox-Ox. In the intermediate main absorbent region 10B, the longitudinal compressed grooves 11, 11 are curved away from the longitudinal centerline Oy-Oy. The rear main absorbent region 10D is elongated longitudinally of the napkin, in which the distance between the longitudinal compressed grooves 11, 11 is smaller than in the intermediate main absorbent region 10B.

Forward of the front transverse compressed groove 12 is provided a front outside compressed groove 14, as shown in FIG. 2. The front outside compressed groove 14 is curved forward and connects the right and left longitudinal compressed grooves 11, 11. Rearward of the rear transverse compressed groove 13 is provided a rear outside compressed groove 16. The longitudinal compressed grooves 11, 11, the rear transverse compressed groove 13, and the rear outside compressed groove 16 are connected together, and both the rear transverse compressed groove 13 and the rear outside compressed groove 16 are curved rearward.

In the sanitary napkin 1, the elongated main absorbent region 10 surrounded by the longitudinal compressed grooves 11, 11, the front transverse compressed groove 12, and the rear transverse compressed groove 13 is raised higher than the remaining region outside it.

On both right and left sides of the front main absorbent region 10A, first outside longitudinal compressed grooves 21, 21 are provided outside and at a distance apart from the longitudinal compressed grooves 11, 11. The first outside longitudinal compressed grooves 21, 21 are also curved toward the longitudinal centerline Oy-Oy, wherein the distance therebetween is smallest near the transverse reference line Ox-Ox.

On both right and left sides of the rear main absorbent region 10D, second outside longitudinal compressed grooves 22, 22 are provided at a distance transversely apart from the longitudinal compressed grooves 11, 11. The second outside longitudinal compressed grooves 22, 22 extend longitudinally in substantially parallel relation to the longitudinal centerline Oy-Oy.

The individual compressed grooves are formed by heating the topsheet 3 and the liquid absorbent layer 6 under pressure from the side of the topsheet 3. At the bottoms of the individual compressed grooves, high-density compressed portions (highly compressed portions) and medium-density compressed portions (portions whose density is slightly lower than the high-density compressed portions) alternate with each other along the linear pattern of the compressed grooves so that the grooves are of a sufficient depth overall.

As shown in FIG. 2, since the sanitary napkin 1 has bilateral symmetry about the longitudinal centerline Oy-Oy, the right and left flaps are of symmetrical shape. Along the transverse reference line Ox-Ox, fold-back flaps 41 are disposed to project transversely outward from the main body 2. Each fold-back flap 41 extends over a given length with center at the transverse reference line Ox-Ox. Rearward of the fold-back flaps 41 are disposed rear flaps 42 also projecting transversely outward from the main body 2; forward of the fold-back flaps 41 are disposed front flaps 43 projecting transversely outward from the main body 2.

On the garment-side surface of the sanitary napkin 1, there are disposed pressure-sensitive adhesive layers, as shown in FIG. 2. The fold-back flap 41 has a front pressure-sensitive adhesive layer 51. The rear flap 42 has first and second rear pressure-sensitive adhesive layers 52, 53 that are separate from each other in the longitudinal direction. Furthermore, central pressure-sensitive adhesive layers 54 are disposed on each side of the longitudinal centerline Oy-Oy. The central pressure-sensitive adhesive layers 54 extend longitudinally in the shape of a strip.

As shown in FIG. 2, the side sheets 4, 4 are disposed on right and left side portions of the skin-side surface 2a of the main body 2, wherein front edges 4f, 4f of the side sheets 4, 4 coincide with the front end edge 1a of the sanitary napkin 1, rear edges 4g, 4g of the side sheets 4, 4 coincide with the rear end edge 1b of the sanitary napkin 1, and side edges 4h, 4h of the side sheets 4, 4 coincide with side edges of the sanitary napkin 1, i.e., edges of the fold-back flaps 41, the rear flaps 42 and the front flaps 43.

As shown in FIG. 5, the side sheet 4 has a single-layer portion and a multi-layer portion 4a. Outside the side edge 6c of the liquid absorbent layer 6, the single-layer portion of the side sheet 4 is bonded to the backsheet 5 through a hot-melt type adhesive. In the fold-back flap 41, as shown in FIG. 5, a reinforcing sheet 56 is interposed between and bonded to the backsheet 5 and the side sheet 4. Also in the rear flap 42, another reinforcing sheet is interposed between and bonded to the backsheet 5 and the side sheet 4.

In the multi-layer portion 4a, the side sheet 4 is folded into two along a fold line 4i and bonded to itself between the fold line 4i and an edge 4j. The multi-layer portion 4a is bonded to the topsheet 3 along the longitudinally extending base 31, as shown in FIG. 5. The base 31 extends over the entire length of the main body 2 in parallel with the longitudinal centerline Oy-Oy. The multi-layer portion 4a has first, second and third intermediate portions (fold lines) 4b, 4d, 4e between the fold line 4i and the base 31.

FIGS. 6(A), 6(B), 7(A) and 7(B) are schematic diagrams showing sections of the leakage preventing wall 30 formed of the multi-layer portion 4a. Here, FIG. 6(A) is a schematic diagram showing the same section as FIG. 5.

FIG. 6(B) is a schematic diagram showing a section taken along line (ii)-(ii) which coincides with an inner edge's front end 32a as shown in FIG. 4. From the inner edge's front end 32a to the front end edge 1a (4f), a lower portion of the multi-layer portion 4a from the base 31 to the first intermediate portion 4b is generally fixed to the topsheet 3 in such a folded state as shown in FIG. 6(B). This fixation may be achieved by applying a hot-melt type adhesive, but if the topsheet 3 and the side sheet 4 are heat-sealed or ultrasonic-sealed under pressure, the folded side sheet 4 can be made thin, preventing irregularities on the skin-side.

FIG. 7(A) is a schematic diagram showing a section taken along line (iii)-(iii) drawn at a position intermediate the inner edge's front end 32a and an outer edge's front end 33a located farther forward than the inner edge's front end 32a. At this intermediate position, an upper portion of the multi-layer portion 4a from the first intermediate portion 4b to the fold line 4i is fixed within a range of a width Wb so as not to move away from the skin-side surface. In FIG. 7(A), 34a indicates an end of the fixed portion of the width Wb. As shown in FIG. 4, the end 34a of the fixed portion extends obliquely from the inner edge's front end 32a to the outer edge's front end 33a.

FIG. 7(B) is a schematic diagram showing a section taken along line (iv)-(iv) which coincides with the outer edge's front end 33a as shown in FIG. 4. At this position, the upper portion of the multi-layer portion 4a from the first intermediate portion 4b to the fold line 4i is generally fixed so as not to move away from the skin-side surface. Between the obliquely extending end 34a and the front end edge 1a (4f) shown in FIG. 4, accordingly, the upper portion of the multi-layer portion 4a is fixed so as not to move away from the skin-side surface. For fixation of the upper portion of the multi-layer portion 4a to the lower portion of the multi-layer portion 4a, heat-sealing technique may be used, but preferably used is an adhesive such as a hot-melt type adhesive.

In the present embodiment, the lower portion of the multi-layer portion 4a from the base 31 to the first intermediate portion 4b is heat-sealed or ultrasonic-sealed together with the topsheet 3 to reduce the thickness of the folded side sheet 4, as shown in FIG. 6(B), while the upper portion of the multi-layer portion 4a from the first intermediate portion 4b to the fold line 4i (which is intended to directly contact the wearer's skin) is bonded through a hot-melt type adhesive, so that even though the folded and bonded side sheet 4 is made thin, it hardly gives the wearer's body a stiff feel due to heat-sealing or ultrasonic-sealing.

More specifically, the lower portion of the multi-layer portion 4a from the base 31 to the first intermediate portion 4b is heat-sealed from the line (ii)-(ii) coinciding with the inner edge's front end 32a to the front end edge 1a (4f), as shown in FIG. 6(B), while the upper portion of the multi-layer portion 4a is bonded through a hot-melt type adhesive from the obliquely extending end 34a to the front end edge 1a (4f).

In FIG. 6(B), the side sheet 4 may be fixed to the topsheet 3 only within a range of a small width Wa from the first intermediate portion 4b to adjacent the third intermediate portion 4e; in FIG. 7(B), the upper portion of the multi-layer portion 4a may be fixed only within a range of a width Wc starting from the fold line 4i. Here, the multi-layer portion 4a may be folded and bonded in any way as long as the first intermediate portion 4b is fixed at the inner edge's front end 32a so as not to move away from the topsheet 3 and the fold line 4i is fixed at the outer edge's front end 33a so as not to move away from the skin-side surface.

For example, the multi-layer portion 4a shown in FIG. 7(B) may be left unfixed to the skin-side surface over a given width Wd from the first intermediate portion 4b. It should be appreciated that the present invention includes even such a structure.

Also in the rear portion of the sanitary napkin 1, the multi-layer portion 4a at an inner edge's rear end 32b is fixed in the same manner as shown in FIG. 6(B) and the multi-layer portion 4a at an outer edge's rear end 33b is fixed in the same manner as shown in FIG. 7(B). At a position intermediate the inner edge's rear end 32b and the outer edge's rear end 33b, the multi-layer portion 4a is fixed in the same manner as shown in FIG. 7(A). At the inner edge's rear end 32b, the first intermediate portion 4b is fixed so as not to move away from the skin-side surface. At the outer edge's rear end 33b, the fold line 4i is fixed so as not to move away from the skin-side surface. The fixed portion has an end 34b extending obliquely from inner edge's rear end 32b to the outer edge's rear end 33b.

Within the range of a length L1 between the outer edge's front end 33a and the outer edge's rear end 33b shown in FIG. 3, the fold line 4i of the multi-layer portion 4a is in a free state. Within the range of a length L2 between the inner edge's front end 32a and the inner edge's rear end 32b, not only the fold line 4i but also the first intermediate portion 4b is in a free state, as shown in FIGS. 5 and 6(A).

Therefore, the multi-layer portion 4a forms the leakage preventing wall 30 over the length L1. In the leakage preventing wall 30, the lower portion of the multi-layer portion 4a from the base 31 to the first intermediate portion 4b is called "rising portion" while the upper portion of the multi-layer portion 4a from the first intermediate portion 4b to the fold line 4i is called "skin-contacting portion". In FIGS. 5 and 6(A), the skin-contacting portion is indicated by 36, while the rising portion includes first, second and third rising portions 35A, 35B, 35D. The first rising portion 35A extends from the base 31 to the third intermediate portion 4e to have an extremely small width. The second rising portion 35B extends from the third intermediate portion 4e to the second intermediate portion 4d. The third rising portion 35D extends from the second intermediate portion 4d to the first intermediate portion 4b. In the skin-contacting portion 36, the fold line 4i is called "outer edge" while the first intermediate portion 4b is called "inner edge". The outer edge and the inner edge are indicated by 36A and 36B, respectively. In the rising portion, on the other hand, the base 31 is called "lower end" while the first intermediate portion 4b is called "upper end".

At the end 34a extending obliquely between the inner edge's front end 32a and the outer edge's front end 33a, the second intermediate portion 4d is fixed to the skin-side surface. Also at the end 34b extending obliquely between the inner edge's rear end 32b and the outer edge's rear end 33b, the second intermediate portion d is fixed to the skin-side surface. In the leakage preventing wall 30 shown in FIGS. 5 and 6(A), accordingly, the second intermediate portion 4d is positioned farther away from the longitudinal centerline Oy-Oy than the first intermediate portion 4b (inner edge 36B).

As shown in FIGS. 5 and 6(A), the multi-layer portion 4a is provided with elastic members 37a, 37b, 37c, 37d, 37e, 37f and 37g. These elastic members are interposed between confronting surfaces of the side sheet 4 and bonded thereto through a hot-melt type adhesive while being kept in a longitudinally elongated state. The elastic members 37a-37g are in parallel with each other and extend longitudinally from a position forward of the outer edge's front end 33a to a position rearward of the outer edge's rear end 33b.

In the multi-layer portion 4a, any number of elastic members may be provided anywhere, but it is preferred that one elastic member is located in or adjacent the outer edge 36A and another elastic member is located in or adjacent the inner edge 36B. In the present embodiment, as shown in FIGS. 5 and 6(A), the elastic member 37a is located in the outer edge 36A as first elastic member, while the elastic member 37d is located in the inner edge 36B as second elastic member. When the sanitary napkin 1 is flattened as shown in FIGS. 2 and 3, it is preferred that the first elastic member (elastic member 37a), which tends to bring the outer edge's front end 33a and the outer edge's rear end 33b closer to each other, exhibits a larger elastic contractive force than the second elastic member (elastic member 37d), which tends to bring the inner edge's front end 32a and the inner edge's rear end 32b closer to each other.

Preferably, the first elastic member (elastic member 37a) exhibits an elastic contractive force at least 1.2 times that of the second elastic member (elastic member 37d). For instance, the elastic contractive force of the first elastic member (elastic member 37a) may be set within the range of 0.5 to 2 N, while the elastic contractive force of the second elastic member (elastic member 37d) may be set within the range of 0.8 to 1.5 N.

The elastic member 37b located closer to the outer edge 36A of the skin-contacting portion 36 may be regarded as a part of the first elastic member, while the elastic member 37c located closer to the inner edge 36B may be regarded as a part of the second elastic member. Also in this case, the elastic contractive force of the first elastic member is preferably larger than the elastic contractive force of the second elastic member.

In order that the first elastic member can exhibit a larger elastic contractive force than the second elastic member, the first and second elastic members with equal modulus of elasticity may be bonded to the multi-layer portion 4a with the first elastic member being elongated more than the second elastic member. If the first elastic member has a larger modulus of elasticity than the second elastic member, on the other hand, they may be bonded to the multi-layer portion 4a at equal elongation.

The elastic member 37f is located in (or adjacent) the second intermediate portion 4d. With the elastic member 37f located in the second intermediate portion 4d, the second intermediate portion 4d in the leakage preventing wall 30 can always be located transversely outward of the inner edge 36B. In addition, the second intermediate portion 4d can easily function as a fold axis. Accordingly, when a body pressure acts on the skin-contacting portion 36, the second rising portion 35B and the third rising portion 35D can easily be folded along the second intermediate portion 4d. Therefore, the skin-contacting portion 36 receiving the body pressure can descend generally vertically toward the main body 2, hardly causing lateral displacement.

With the elastic member 37g located in the third intermediate portion 4e, the third intermediate portion 4e can also function as a fold axis.

In the sanitary napkin 1, an elastic contractive force is exerted between the outer edge's front end 33a and the outer edge's rear end 33b to bring them closer to each other and an elastic contractive force is also exerted between the inner edge's front end 32a and the inner edge's rear end 32b to bring them closer to each other. When the sanitary napkin 1 is not compressed flat and left in a free state, therefore, the skin-side surface 2a is concavely deformed as shown in FIG. 1, so that the leakage preventing walls 30 rise from the skin-side surface 2a.

As shown in FIG. 3, since the outer edge's front end 33a is located farther forward than the inner edge's front end 32a, the outer edge's rear end 33b is located farther rearward than the inner edge's rear end 32b, and the length L1 between the outer edge's front end 33a and the outer edge's rear end 33b is larger than the length L2 between the inner edge's front end 32a and the inner edge's rear end 32b, the skin-contacting portion 36 is tensioned with the outer edge 36A located closer to the wearer's skin than the inner edge 36B. In other words, the skin-contacting portion 36 is inclined with the outer edge 36A located higher than the inner edge 36B.

With the length L1 being set sufficiently longer than the length L2, the skin-contacting portion 36 can be inclined as described above. In this construction, if the first elastic member exhibits a larger elastic contractive force than the second elastic member, the outer edge's front end 33a and the outer edge's rear end 33b can be attracted more strongly to each other. As a result, the outer edge 36A can be certainly raised toward the wearer's skin higher than the inner edge 36B, so that the angle of inclination of the skin-contacting portion 36 can be set large anywhere.

Here, the length L2 is preferably 50 to 95% of the length L1. If the length L2 over which the inner edge 36B of the skin-contacting portion 36 is allowed to move away from the skin-side surface 2a of the main body 2 is smaller than the lower limit, the allowable rising height of the whole leakage preventing wall 30 will be decreased. If the length L2 is greater than the upper limit, on the other hand, the skin-contacting portion 36 will be difficult to incline as described above.

In the sanitary napkin 1 according to the present embodiment, furthermore, since the longitudinal compressed grooves 11, 11 and the first outside longitudinal compressed grooves 21, 21 are formed in the skin-side surface 2a between the right and left leakage preventing walls 30, 30, the main body 2 tends to be folded along the compressed grooves 11, 21. Since the elastic members 37a-37g exert an elastic contractive force outside the first outside longitudinal compressed grooves 21, 21, the main body 2 tends to be deformed such that both side portions on which the leakage preventing walls 30, 30 are disposed rise toward the wearer's body, as shown in FIG. 6(A). Such a deformation of the main body 2 as shown in FIG. 6(A) may result in a further increase in the angle of inclination of the skin-contacting portion 36.

The leakage preventing walls 30, 30 need be located at least on both sides of the front main absorbent region 10A that is intended to face the vaginal opening, wherein the length L1 is preferably equal to or greater than 60 mm, more preferably equal to or greater than 80 mm. In the present embodiment, the leakage preventing walls 30, 30 are sufficiently long to conform to the wearer's body from both sides of the vaginal opening, via both sides of the anus, to both sides of the cleft of the buttocks. In this case, the upper limit of the length L1 is 350 mm, preferably 250 mm.

When the sanitary napkin 1 is in a free state, the allowable rising height of the leakage preventing wall 30 as measured from the base 31 to the outer edge 36A is preferably 8 to 50 mm, more preferably 10 to 30 mm. On the other hand, the width of the skin-contacting portion 36 is preferably 3 to 30 mm, more preferably 5 to 15 mm. The right and left leakage preventing walls 30, 30 may have a distance of 50 to 80 mm between the inner edges 36B, 36B. The present invention should not be construed as limited to the foregoing ranges, but if the individual dimensions are set within the foregoing ranges, the skin-contacting portion 36 during wear can easily be kept in contact with the wearer's body on both sides of the vaginal opening, effectively preventing leakage. In addition, even if the leakage preventing walls 30 subjected to the body pressure fall to the skin-side surface 2a, they will not widely cover the area having the liquid absorbent layer 6.

Next, preferred examples of the individual components of the sanitary napkin 1 will be described.

The topsheet 3 is a liquid-permeable sheet, such as a through-air bonded nonwoven fabric, a spunlaced nonwoven fabric, or an apertured resin film (resin film formed with a large number of liquid passage holes). The backsheet 5 is a resin film that is impermeable to liquid but may be breathable.

The liquid absorbent layer 6 may be a layer of pulp, a layer of pulp and superabsorbent polymer, or an air-laid nonwoven fabric in which only pulp or pulp and rayon are deposited by air-laid process and the fibers are fixed together through an adhesive. The liquid permeable layer 7 is a bulky nonwoven fabric of a three-dimensional network structure, such as a through-air bonded nonwoven fabric or an air-laid nonwoven fabric in which pulp and synthetic fibers are deposited by air-laid process and the fibers are fixed together through an adhesive.

The side sheet 4 is impermeable to liquid and is preferably treated to be water-repellent. The side sheet 4 may be a through-air bonded nonwoven fabric, a point-bonded nonwoven fabric, a meltblown nonwoven fabric, a spunbonded nonwoven fabric, a laminated composite of spunbond/meltblown/spunbond or the like. Alternatively, there may be used a resin film, such as polyethylene or polypropylene, whose skin-contacting surface is covered with one of the above-mentioned nonwoven fabrics.

The elastic members 37a-37g may be of a rubber material such as polyurethane, polybutadiene or isoprene, ethylene-vinyl acetate copolymer, or an elastic polymer such as polyolefin, and they may be used in the form of a yarn, filament or strip. For instance, polyurethane elastic yarns of a fineness of 470 dtex may be fixed to the side sheet 4 while being elongated 1.5 times.

Hereinbelow, the function of the sanitary napkin will be described.

FIG. 1 shows a state where the sanitary napkin 1 is attached to an undergarment 60 such as a sanitary panty. The undergarment 60 has leg openings 61, 61. Between a front body 62 and a rear body 63, the undergarment 60 has a crotch part 64 on which the front portion of the sanitary napkin 1 is placed.

Through the central pressure-sensitive adhesive layers 54, the garment-side surface 2b of the main body 2 is adhered to the inner surface of the undergarment 60 from the crotch part 64 to the lower part of the back body 63. The fold-back flaps 41 are folded back along the side edges of the crotch part 64 and the front pressure-sensitive adhesive layers 51 on the fold-back flaps 41 are adhered to the outer surface of the crotch part 64. The rear flaps 42 kept in a developed state are adhered to the inner surface of the lower part of the back body 63 through the first rear pressure-sensitive adhesive layers 52 and the second rear pressure-sensitive adhesive layers 53.

When the undergarment 60 is worn, the longitudinal central portion of the front main absorbent region 10A, i.e., the intersection of the longitudinal centerline Oy-Oy and the transverse reference line Ox-Ox and its surrounding area may come into contact with the woman's vaginal opening, the intermediate portion between the front main absorbent region 10A and the intermediate main absorbent region 10B may confront the perineum, and the intermediate main absorbent region 10B may confront the anus. Accordingly, the rear main absorbent region 10D may extend along the cleft of the buttocks.

Figure 10:
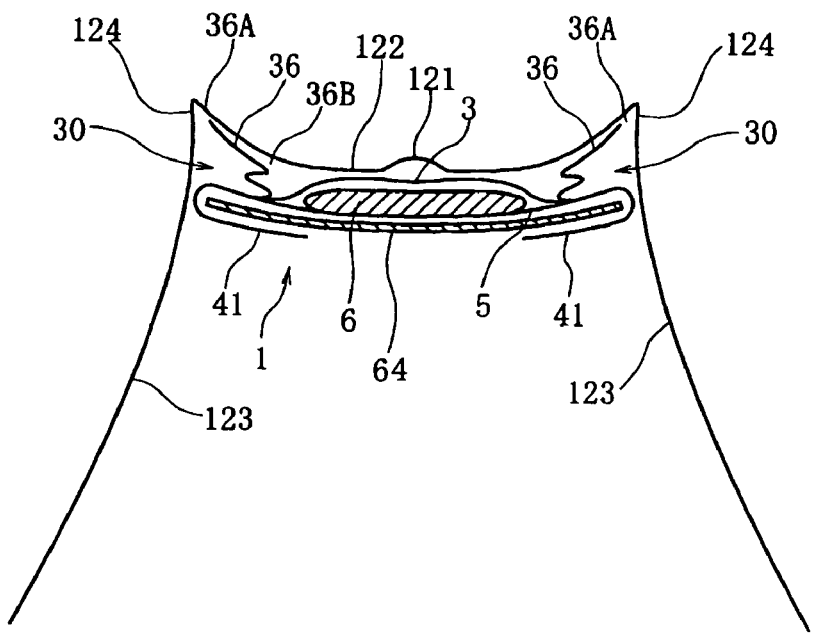
FIG. 10 is a schematic diagram showing a state where the sanitary napkin according to the first embodiment of the present invention is put on the wearer's crotch.
Figure 11:
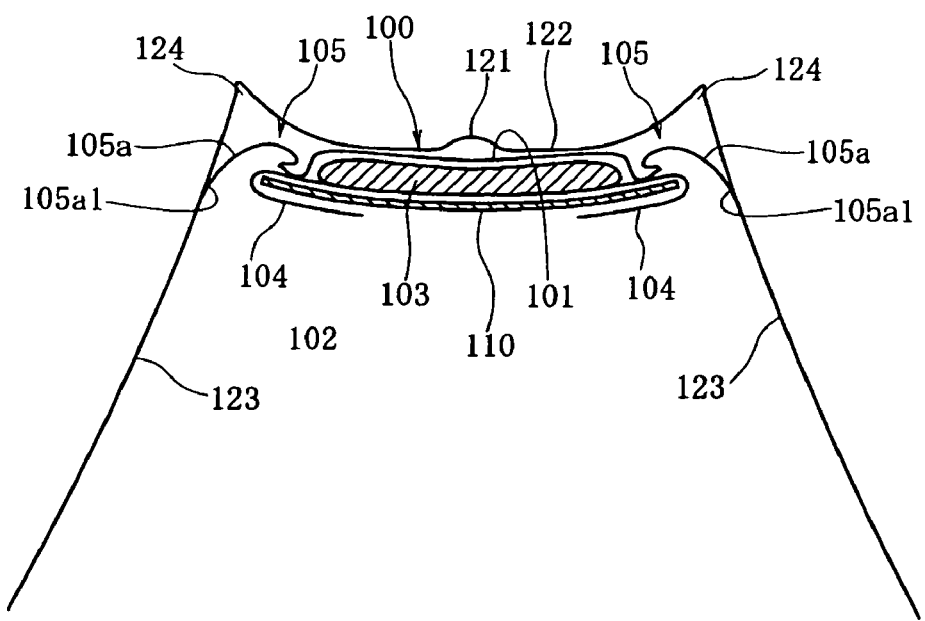
FIG. 11 is a schematic diagram showing a state where a conventional sanitary napkin is put on the wearer's crotch.

FIG. 10 shows a state where the sanitary napkin 1 is put on the woman's crotch. In the woman's crotch, 121 represents the vaginal opening, 122 represents the labia majora, 123 represents the thigh, and 124 represents a narrow depression between the thigh 123 and the abdomen.

When the sanitary napkin 1 is put on, the leakage preventing walls 30, 30 confront the wearer's body on both sides of the vaginal opening. At this time, since the skin-contacting portions 36, 36 are inclined with the outer edges 36A, 36A located closer to the wearer's skin than the inner edges 36B, 36B, the skin-contacting portions 36, 36 easily come into face-to-face contact with the wearer's crotch to conform to the bulges on both sides of the vaginal opening 121. Moreover, the skin-contacting portions 36, 36 can easily enter the depressions 124, 124, hardly leaving a space between the depressions 124, 124 and the leakage preventing walls 30, 30.

Menstrual blood discharged from the vaginal opening 121, which usually passes through the topsheet 3 for subsequent absorption by the liquid absorbent layer 6, may sometimes flow down the wearer's crotch to the right and left sides without being absorbed by the liquid absorbent layer 6. Even in this case, the menstrual blood can be blocked by the skin-contacting portions 36, 36, hardly reaching the thighs 123, 123. In addition, since the skin-contacting portions 36, 36 extend from both sides of the vaginal opening 121 toward the buttocks with their outer edges 36A, 36A inserted in the depressions 124, 124, the menstrual blood hardly flows down the depressions 124, 124 anteriorly or posteriorly. Accordingly, the menstrual blood blocked by the leakage preventing walls 30, 30 can be returned to the topsheet 3 through the skin-contacting portions 36, 36 for subsequent absorption by the liquid absorbent layer 6.

As has been described hereinabove, the sanitary napkin 1 is effective in preventing lateral and rearward leakage of menstrual blood.

Figure 8:
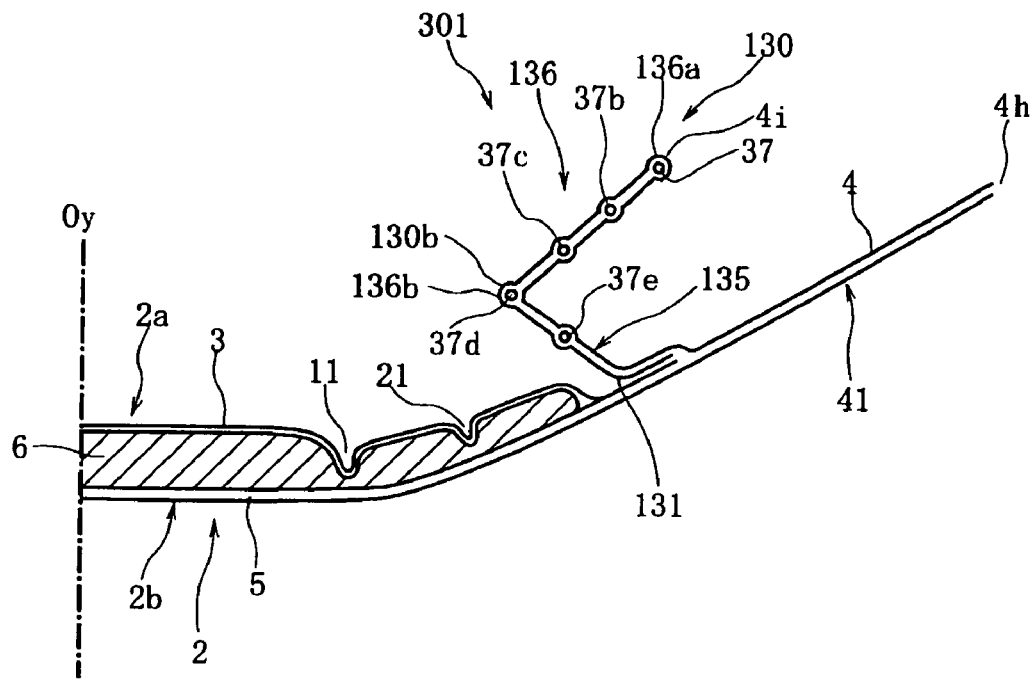
FIG. 8 is a schematic diagram corresponding to FIG. 6(A), showing a modification of the first embodiment.

FIG. 8 is a schematic diagram corresponding to FIG. 6(A), showing a sanitary napkin 301 as a modification of the sanitary napkin 1 according to the first embodiment.

The sanitary napkin 301 has the main body 2 identical in shape and construction to that of the sanitary napkin 1 according to the first embodiment. The sanitary napkin 301 is provided on right and left side portions of the main body 2 with the side sheets 4, 4. The multi-layer portion 4a of the side sheet 4 forms a leakage preventing wall 130.

In the leakage preventing wall 130, the portion extending from a base (lower end) 131 to an intermediate portion (upper end) 130b is a rising portion 135, while the portion extending from the intermediate portion 130b to the fold line 4i is a skin-contacting portion 136. The fold line 4i is an outer edge 136a of the skin-contacting portion 136 and the intermediate portion 130b is an inner edge 136b of the skin-contacting portion 136. In the multi-layer portion 4a of the side sheet 4, the elastic members 37a-37e are fixed. The first elastic member (elastic member 37a) is provided to exhibit a larger elastic contractive force than the second elastic member (elastic member 37d).

Also in the sanitary napkin 301, the inner edge 136b is fixed to the skin-side surface at the inner edge front edge 32a and the inner edge rear edge 32b shown in FIGS. 2 and 3 and the outer edge 136a is fixed to the skin-side surface at the outer edge front edge 33a and the outer edge rear edge 33b. Accordingly, the skin-contacting portion 136 can be inclined with the outer edge 136a raised closer to the wearer's skin than the inner edge 136b.

Figure 9:
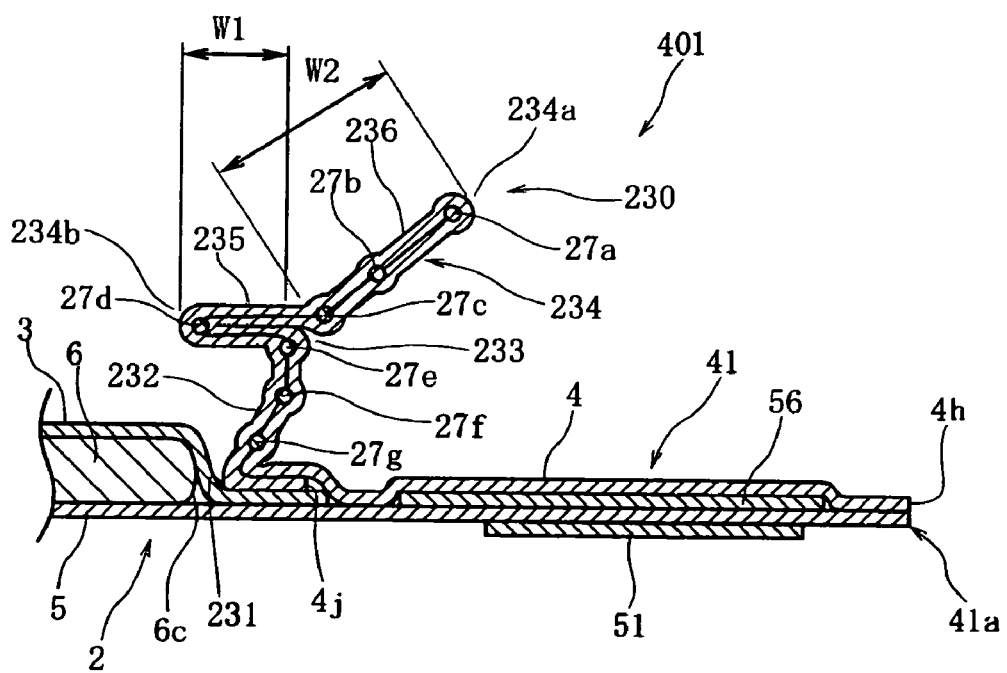
FIG. 9 is a sectional view corresponding to FIG. 5, showing a sanitary napkin according to a second embodiment of the present invention.

FIG. 9 is a sectional view corresponding to FIG. 5, showing a sanitary napkin 401 according to a second embodiment of the present invention.

The sanitary napkin 401 has the main body 2 identical in shape and construction to that of the sanitary napkin 1 according to the first embodiment. The sanitary napkin 401 is provided on right and left side portions of the main body 2 with the side sheets 4, 4. The multi-layer portion 4a of the side sheet 4 forms a leakage preventing wall 230. The leakage preventing wall 230 has a rising portion 232 rising from a base (lower end) 231 and a skin-contacting portion 234 above a boundary 233 that is an upper end of the rising portion 232.

The skin-contacting portion 234 has an inner edge 234b and an outer edge 234a. Of the skin-contacting portion 234: the inner portion extending from the inner edge 234b to the boundary 233 with a width W1 is indicated by 235; the outer portion extending from the boundary 233 to the outer edge 234a with a width W2 is indicated by 236. In the inner portion 235, the multi-layer portion 4a is further folded into two and fixed together. This fixation is preferably achieved by applying a hot-melt type adhesive so as not to give a stiff feel to the wearer's skin. Since the inner portion 235 thus bonded together is of four thicknesses of the side sheet 4, the inner portion 235 has a higher stiffness than the outer portion 236.

In the multi-layer portion 4a forming the leakage preventing wall 230, elastic members 27a, 27b, 27c, 27d, 27e, 27f, 27g are fixed between confronting surfaces of the side sheet 4. In the multi-layer portion 4a, any number of elastic members may be provided anywhere, but it is preferred that one elastic member is located in or adjacent the outer edge 234a of the skin-contacting portion 234 and another elastic member is located in or adjacent the inner edge 234b. In the present embodiment, the elastic member 27a is located in the outer edge 234a as first elastic member, while the elastic member 27d is located in the inner edge 234b as second elastic member. It is also preferred that the elastic member 27e is located in the boundary 233. With the elastic members being thus located, the leakage preventing wall 230 in a free state can easily be kept in a rising position as shown in FIG. 9.

Preferably, the first elastic member (elastic member 27a) located in the outer edge 234a exhibits a larger elastic contractive force than the second elastic member (elastic member 27d and elastic member 27c).

Also in the sanitary napkin 401, the inner edge 234b is fixed to the skin-side surface at the inner edge front edge 32a and the inner edge rear edge 32b shown in FIGS. 2 and 3 and the outer edge 234a is fixed to the skin-side surface at the outer edge front edge 33a and the outer edge rear edge 33b.

In the leakage preventing wall 230, the side sheet 4 is folded more times in the inner portion 235 to increase stiffness, so that even though the length of the leakage preventing wall 230 differs between along the inner edge 234b and along the boundary 233, the inner portion 235 is not inclined steeply. On the other hand, since the outer portion 236 is not so stiff and the first elastic member (elastic member 27a) can exhibit a larger elastic contractive force, the outer portion 236 can be inclined with the outer edge 234a raised closer to the wearer's skin, so that the angle of inclination of the outer portion 236 is larger than that of the inner portion 235.

When the sanitary napkin 401 is put on, therefore, the inner portions 235 easily come into face-to-face contact with the wearer's crotch on both sides of the vaginal opening, while the inclined outer portions 236 easily enter the depressions 124 at the root ends of the thighs 123 shown in FIG. 10.

The inner wall 125, in which the multi-layer portion 4a is further folded into two and bonded together as shown in FIG. 9, may extend over the entire length of the leakage preventing wall 230. Alternatively, it may be formed only on both sides of the front main absorbent region 10A, for example, within a range of ±30 mm longitudinally from the transverse reference line Ox-Ox. In this case, the remaining portions of the leakage preventing wall 230 may be constructed as shown in FIG. 5 or 8.

The preferred allowable rising height of the leakage preventing wall 230 is equal to that in the sanitary napkin 1 according to the first embodiment.

However, the width W1 of the inner portion 235 shown in FIG. 9 is preferably 20 to 50% of the sum of the width W1 and the width W2 of the outer portion 236. For example, the width W1 is preferably 3 to 15 mm, more preferably 5 to 10 mm. On the other hand, the width W2 is preferably 5 to 20 mm, more preferably 5 to 15 mm. The preferred width of the skin-contacting portion 234 is equal to that in the first embodiment.

With the width W2 of the outer portion 236 being larger than the width W1 of the inner portion 235, the steeply inclined outer portions 236 can easily enter the depressions 124 on both sides of the vaginal opening.

According to the present invention, as has been described hereinabove, there is provided a sanitary napkin effective in preventing lateral and rearward leakage of menstrual blood, in which leakage preventing walls can be kept in close contact with the wearer's crotch.

Although the present invention has been illustrated and described with respect to exemplary embodiments thereof, it should be understood by those skilled in the art that the foregoing and various other changes, omission and additions may be made therein and thereto, without departing from the spirit and scope of the present invention. For example, the present invention may be embodied not only in such an elongated sanitary napkin but also in a sanitary napkin symmetrical about the transverse reference line Ox-Ox. Therefore, the present invention should not be understood as limited to the specific embodiments set out above but to include all possible embodiments which can be embodied within a scope encompassed and equivalent thereof with respect to the features set out in the appended claims.

What is claimed is:

1. A sanitary napkin comprising:
    an elongated main body having a skin-side surface and a garment-side surface and including a liquid absorbent layer; and
    a pair of leakage preventing walls disposed on the skin-side surface of the main body and extending longitudinally of the main body in parallel with each other,
    each leakage preventing wall being composed of a sheet and a plurality of longitudinally extending elastic members for exerting an elastic contractive force on the sheet and including:
        a rising portion with a lower end fixed to the skin-side surface of the main body; and
        a skin-contacting portion contiguous to an upper end of the rising portion, the skin-contacting portion having transversely opposing outer and inner edges, the inner edge being a boundary between the rising portion and the skin-contacting portion and located closer to a longitudinal centerline of the sanitary napkin than the outer edge,
        longitudinally opposing front and rear ends of the inner edge, and
        longitudinally opposing front and rear ends of the outer edge being fixed to the skin-side surface of the main body, and
        the elastic members include first and second elastic members located in the outer and inner edges, respectively, and at least one additional elastic member located between the first and second elastic members,
    wherein a length between the front and rear ends of the outer edge is larger than a length between the front and rear ends of the inner edge, such that the leakage preventing wall rises with the outer edge moved farther away from the skin-side surface of the main body than the inner edge when the sanitary napkin assumes an uncompressed, free state,
    wherein along a straight line between the front end of the inner edge and the front end of the outer edge and along a straight line between the rear end of the inner edge and the rear end of the outer edge, the rising portion and the skin-contacting portion are fixed to the skin-side surface of the main body with an intermediate portion thereof of the rising portion folded in two to have a longitudinally extending fold line directed transversely outwardly over an entire length of the rising portion,
    wherein the skin-contacting portion is unattached to the skin-side surface of the main body substantially entirely along a longitudinal extent of the leakage preventing wall between the straight line between the front end of the inner edge and the front end of the outer edge and the straight line between the rear end of the inner edge and the rear end of the outer edge,
    wherein each of the straight line between the front end of the inner edge and the front end of the outer edge and the straight line between the rear end of the inner edge and the rear end of the outer edge extends obliquely outwardly in a transverse direction from the inner edge to the outer edge, and
    wherein when the main body is flattened, the first elastic member exerts a larger elastic contractive force than the second elastic member.

2. A sanitary napkin according to claim 1, wherein the front end of the outer edge is located farther forward than the front end of the inner edge, and the rear end of the outer edge is located farther rearward than the rear end of the inner edge.

3. A sanitary napkin according to claim 1, wherein the length between the front and rear ends of the inner edge is 50 to 95% of the length between the front and rear ends of the outer edge.

4. A sanitary napkin according to claim 1, wherein fixation of the rising portion to the skin-side surface of the main body is performed by heat-sealing, while fixation of the skin-contacting portion to the skin-side surface of the main body is performed by bonding with a hot-melt type adhesive.

5. A sanitary napkin comprising:
    an elongated main body having a skin-side surface and a garment-side surface and including a liquid absorbent layer; and
    a pair of leakage preventing walls disposed on the skin-side surface of the main body and extending longitudinally of the main body in parallel with each other,
    each leakage preventing wall being composed of a sheet and a plurality of longitudinally extending elastic members for exerting an elastic contractive force on the sheet and including:
        a rising portion with a lower end fixed to the skin-side surface of the main body: and
        a skin-contacting portion contiguous to an upper end of the rising portions the skin-contacting portion having transversely opposing outer and inner edges, the inner edge being located closer to a longitudinal centerline of the sanitary napkin than the outer edge,
        longitudinally opposing front and rear ends of the inner edge being fixed to the skin-side surface of the main body, and
        longitudinally opposing front and rear ends of the outer edge being fixed to the skin-side surface of the main body, and
    the elastic members including first and second elastic members located in the outer and inner edges, respectively, and at least one additional elastic member located between the first and second elastic members,
    wherein along a straight line between the front end of the inner edge and the front end of the outer edge and along a straight line between the rear end of the inner edge and the rear end of the outer edge, the rising portion and the skin-contacting portion are fixed to the skin-side surface of the main body with an intermediate portion thereof of the rising portion folded in two to have a longitudinally extending fold line directed transversely outwardly over an entire length of the rising portion,
    wherein the skin-contacting portion is unattached to the skin-side surface of the main body substantially entirely along a longitudinal extent of the leakage preventing wall between the straight line between the front end of the inner edge and the front end of the outer edge and the straight line between the rear end of the inner edge and the rear end of the outer edge,
    wherein each of the straight line between the front end of the inner edge and the front end of the outer edge and the straight line between the rear end of the inner edge and the rear end of the outer edge extends obliquely outwardly in a transverse direction from the inner edge to the outer edge, and
    wherein when the main body is flattened, the first elastic member exerts a larger elastic contractive force than the second elastic member.

6. A sanitary napkin according to claim 5, wherein when the leakage preventing wall is in a rising position, the outer edge is farther away from the skin-side surface of the main body than the upper end of the rising portion so that an outer portion of the skin-contacting portion between the upper end of the rising portion and the outer edge of the skin-contacting portion is inclined.

7. A sanitary napkin according to claim 6, wherein an inner portion of the skin-contacting portion between the upper end of the rising portion and the inner edge of the skin-contacting portion is folded against an upper portion of the rising portion.

8. A sanitary napkin according to claim 6, wherein the outer portion has a larger width than an inner portion of the skin-contacting portion between the upper end of the rising portion and the inner edge of the skin-contacting portion.

9. A sanitary napkin according to claim 5, wherein fixation of the rising portion to the skin-side surface of the main body is performed by heat-sealing, while fixation of the skin-contacting portion to the skin-side surface of the main body is performed by bonding with a hot-melt type adhesive.

10. A sanitary napkin according to claim 5, wherein a length between the front and rear ends of the outer edge is larger than a length between the front and rear ends of the inner edge, such that the leakage preventing wall rises with the outer edge moved farther away from the skin-side surface of the main body than the inner edge when the sanitary napkin assumes an uncompressed, free state, and wherein the upper end of the rising portion is located between the inner edge and the outer edge of the skin-contacting portion so that the skin-contacting portion has an inner portion extending from the upper end to the inner edge and an outer portion extending from the upper end to the outer edge.

* * * * *